United States Patent [19]

Kishida et al.

[11] Patent Number: 5,021,768
[45] Date of Patent: Jun. 4, 1991

[54] DETECTOR FOR DETECTING RESISTANCE BETWEEN FINGERS

[75] Inventors: Toshio Kishida; Chiharu Mori, both of Tsurugashima, Japan

[73] Assignee: ITO Co., Ltd., Tokyo, Japan

[21] Appl. No.: 298,182

[22] Filed: Jan. 17, 1989

[30] Foreign Application Priority Data

Aug. 10, 1988 [JP] Japan ............................... 63-199097

[51] Int. Cl.⁵ ............................................. G08B 21/00
[52] U.S. Cl. .................................... 340/573; 128/734; 273/460; 273/161
[58] Field of Search ........................ 340/573; 128/734; 273/161, 1 E

[56] References Cited

U.S. PATENT DOCUMENTS 3,648,686  3/1972  Payne ................................... 128/734
3,870,034  3/1975  James ................................... 128/734

Primary Examiner—Glen R. Swann, III
Attorney, Agent, or Firm—Kane, Daslimer, Sullivan, Kurucz, Levy, Eisele and Richard

[57] ABSTRACT

A detector detects the variation of resistance between fingers of a human's hands which varies in response to his mental condition. When the mental condition is varied and the resistance between fingers is changed, the detector detects such resistance variation, which is then converted into an electric signal. This electric signal drive light emitting diodes (LEDs) or the like so that the user of this detector can realize his mental condition by watching the light. By further providing a lamp, an image film and a lens, the user can watch the image on the image film when light radiated from the lamp projects such image onto the lens. This detector is useful for meditation and mental training because the user can realize the variation of his mental condition by watching the light or image.

5 Claims, 1 Drawing Sheet

DETECTOR FOR DETECTING RESISTANCE BETWEEN FINGERS

BACKGROUND OF THE INVENTION

1. Field of the Invention

The present invention relates to a detector for detecting resistance between fingers of human, and more particularly to a detector in which resistance variation occurred between fingers of human is detected and then the detected resistance variation is converted into an electric signal for driving an indicator.

2. Prior Art

The conventionally known detector detects and biologically feeds back the resistance between fingers of human to thereby generate some sounds for alarm etc. However, there is no conventional detector whose detection result turns on or off a light emitting diode (LED) etc. In fact, such conventional bio-feedback type detector is disadvantageous in that a man who sits in meditation for mental training must be mentally disturbed by its sound.

SUMMARY OF THE INVENTION

It is accordingly a primary object of the present invention to provide a detector for detecting resistance between fingers by which the light is turned on or off in order to inform its user of the resistance variation occurring between his fingers.

In an aspect of the invention, there is provided a detector for detecting resistance between fingers comprising:

(a) detecting means for detecting resistance between fingers of human's hands, the resistance varying over time;

(b) converting means for converting the variation of the resistance between fingers into an electric signal; and (c) indicator means which is driven to be turned on or off by the electric signal.

BRIEF DESCRIPTION OF THE DRAWINGS

Further objects and advantages of the present invention will be apparent from the following description, reference being had to the accompanying drawings wherein a preferred embodiment of the present invention is clearly shown.

In the drawings.

DESCRIPTION OF A PREFERRED EMBODIMENT

Figure 1:
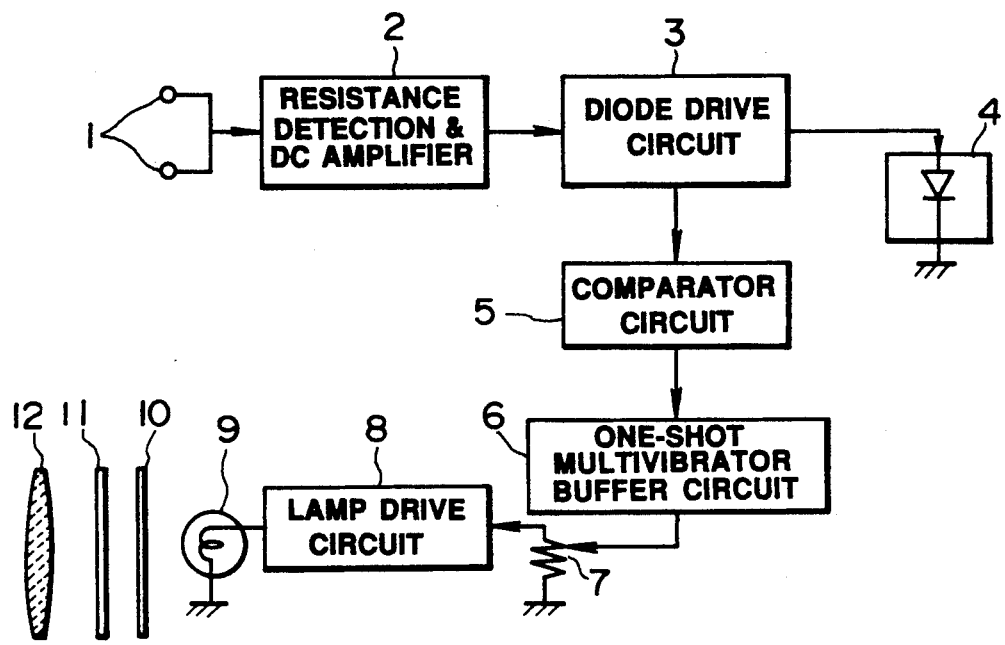
FIG. 1 is a block diagram of an electric circuit of a detector for detecting resistance between fingers according to an embodiment of the present invention.

Referring now to the drawings, wherein like reference characters designate like or corresponding parts throughout the several views, FIG. 1 shows the electric circuit of the detector for detecting resistance between fingers according to an embodiment of the present invention.

In FIG. 1, 1 designates electrodes both connected to a circuit 2 which functions as a resistance detection circuit and a dc amplifier circuit. This circuit 2 is connected to a diode (e.g., LED) 4 which is turned on or off via a diode drive circuit 3. In addition, the diode drive circuit 3 is connected to a comparator circuit 5. In the present embodiment, the output level of this comparator circuit 5 becomes equal to "H" level when the diode 4 is turned on, while this output level becomes equal to "L" level when the diode 4 is turned off.

The comparator circuit 5 is connected to a variable resistor 7 via a one-shot multivibrator buffer circuit 6, and this variable resistor 7 is further connected to a lamp drive circuit 8 for driving and controlling the brightness of a lamp 9. The light emitted from this lamp 9 is diverged into uniform light by a white filter 10, and such uniform light is projected to a slide film 11 on which certain image is printed. This certain image is magnified by a lens 12.

Figure 2:
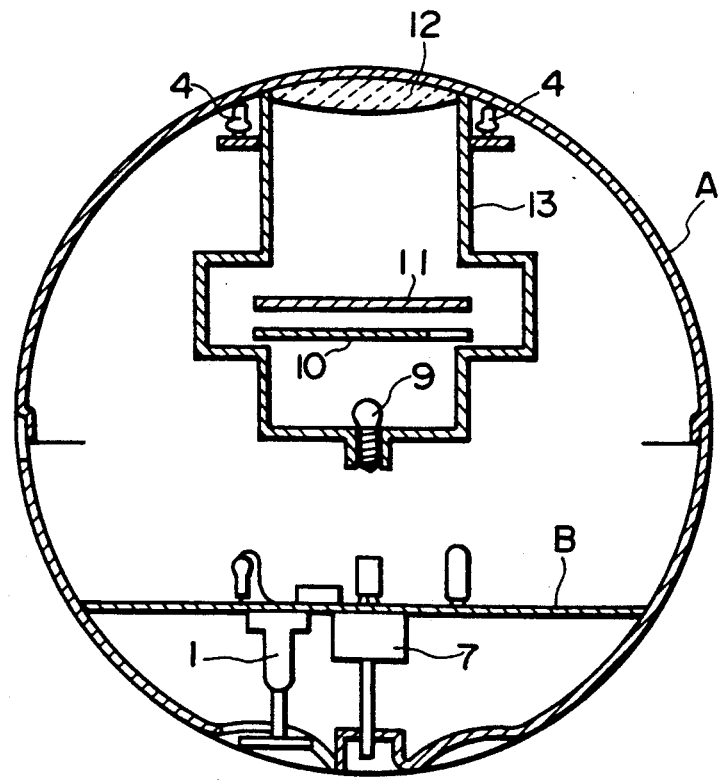
FIG. 2 is a sectional view showing a meditation training device to which the detector for detecting resistance between fingers shown in FIG. 1 is applied.

FIG. 2 shows the meditation training device whose appearance is formed by a main unit A having a hollow ball shape. In addition, a printed circuit board B on which the variable resistor 7 is arranged is inserted into the main unit A. Further, a unit 13 is arranged and mounted on main unit A separate from board B, such that unit 13 can be installed and removed independently of board B. In the upper portion of the main unit A, plural LEDs 4 are arranged in order to indicate the resistance between fingers.

Within the unit 13, the lamp 9, white filter 10, slide film 11 and lens 12 are arranged in the predetermined order such that the light emitted from the lamp 9 can sequentially pass through the white filter 10 and slide film 11. Then, the image on the slide film 11 is magnified by the lens 12.

Further, the electrodes 1, which are arranged in the bottom portion of main unit A, partially stretch to the outside of main unit A such that these electrodes 1 can be easily touched by the finger tips of a user.

Next, a description will be given of the operation of the present embodiment.

First, the user of this meditation training device shown in FIG. 2 holds the ball-shaped main unit A in his crossing hands, and then the user calms down his breath and sits in meditation. When the finger tips of the user's crossing hands touch the electrodes 1, the resistance between the fingers is applied to the circuit 2. The initially detected resistance is set as an initial value. Even if the resistance between fingers depends on the person, this initial value will vary over time. Then, the resistance variation is converted into a dc voltage whose variation is then applied to the diode drive circuit 3. Thus, the LEDs 4 are sequentially turned on or off in response to those input levels. Therefore, if the range of resistance between fingers of each user is set in advance, the LEDs 4 can indicate the resistance between fingers of each user. The comparator circuit 5 compares its input level (corresponding to the present resistance between fingers) with the set level (or the initial value). The comparator circuit 5 outputs the "H" level signal to thereby turn on the lamp 9 when its input level exceeds the set level, while the comparator circuit 5 outputs the "L" level signal to thereby turn off the lamp 9 when its input level is lower than the set level, for example.

The output of comparator circuit 5 drives the one-shot multivibrator buffer circuit 6 on or off, and the output level of this circuit 6 can be varied by the variable resistor 7. Such varied output is supplied to the lamp drive circuit 8 so that the lamp 9 is turned on.

As described before, the light emitted from the lamp 9 is diverged into the uniform light by the white filter 10. This uniform light is projected to the slide film 11 so that the image on the slide film 11 will be magnified by the lens 12.

As described heretofore, even if the user closes his eyes in the meditation, the lamp 9 when turned bright enough so that the user can tell when the lamp is on and thus when the resistance between fingers exceeds the set value.

Meanwhile, when the image of Buddha is on the slide film 11, this image of Buddha is magnified by the lens 12 when the lamp 9 is lighted on. In addition, the brightness of the light of lamp 9 can be adjusted by controlling the variable resistor 7. In this case, when the user half-closes his eyes in the meditation, he can watch the image of Buddha if his resistance between fingers exceeds the setting level. As described heretofore, the user can confirm his mental condition and achievement of meditation training by the light radiated from the meditation training device which employs the detector according to the present invention.

This invention may be practiced or embodied in still other ways without departing from the spirit or essential character thereof. For example, the electric circuit of the present invention is not limited to that as shown in FIG. 1. In addition, the light radiating means is not limited to the LEDs 4 and lamp 9. Of course, other light radiating means can be applied to the present invention. Therefore, the preferred embodiment described herein is illustrative and not restrictive, the scope of the invention being indicated by the appended claims and all variations which come within the meaning of the claims are intended to be embraced therein.

What is claimed is:

1. A detector for detecting resistance between fingers to determine the mental condition of a human, said detector comprising:
   a. detecting means for detecting resistance between fingers of a human's hand, said resistance varying in response to a variation of said human's mental condition;
   b. converting means for converting the variation of said resistance into an electric signal; and
   c. visual indicator means which is turned on or off by said electric signal, said visual indicator means including a light source, a film and a lens which are disposed linearly in a direction toward the eyes of the human, said film having an arbitrary image thereon and being inserted at a position between said light source and said lens so that said image of film is lighted by said light source and then magnified by said lens, whereby said variation of human's mental condition is indicated by visual inspection of said visual indicator means.

2. A detector for detecting resistance between fingers according to claim 1 wherein said indicator generates light in response to said electric signal, the brightness of light radiated from said indicator means being arbitrarily set or varied.

3. A detector for detecting resistance between fingers according to claim 1 wherein said indicator means is a light emitting diode (LED).

4. A detector for detecting resistance between fingers according to claim 1 further comprising comparator means for comparing a predetermined value with said resistance detected by said detecting means to thereby vary its output level, said output level of said comparator means corresponding to turn-on and turn-off operations of said indicator means,
   whereby the output of said comparator means drives said light source to be turned on or off.

5. The detector of claim 1 wherein said converting means includes a comparator means for comparing said resistance to a preselected value.

* * * * *